(12) United States Patent
He et al.

(10) Patent No.: US 12,297,320 B2
(45) Date of Patent: May 13, 2025

(54) POLYETHYLENE GLYCOL DERIVATIVE, PREPARATION METHOD THEREOF, AND POLYETHYLENE GLYCOL HYDROGEL CAPABLE OF PRODUCING A RAPID CROSSLINKING REACTION

(71) Applicant: Changchun Institute of Applied Chemistry Chinese Academy of Sciences, Changchun (CN)

(72) Inventors: Chaoliang He, Changchun (CN); Zhen Zhang, Changchun (CN); Hui Ren, Changchun (CN); Xuesi Chen, Changchun (CN)

(73) Assignee: Changchun Institute of Applied Chemistry Chinese Academy of Sciences, Changchun (CN)

( * ) Notice: Subject to any disclaimer, the term of this patent is extended or adjusted under 35 U.S.C. 154(b) by 739 days.

(21) Appl. No.: 17/619,402

(22) PCT Filed: Jun. 29, 2020

(86) PCT No.: PCT/CN2020/098863
§ 371 (c)(1),
(2) Date: Dec. 15, 2021

(87) PCT Pub. No.: WO2021/237864
PCT Pub. Date: Dec. 2, 2021

(65) Prior Publication Data
US 2023/0002554 A1    Jan. 5, 2023

(30) Foreign Application Priority Data
May 26, 2020    (CN) .......................... 202010455951.3

(51) Int. Cl.
*C08G 65/333* (2006.01)
*C08J 3/075* (2006.01)

(52) U.S. Cl.
CPC . *C08G 65/33337* (2013.01); *C08G 65/33327* (2013.01); *C08G 65/33396* (2013.01);
(Continued)

(58) Field of Classification Search
CPC ....................................................... C08J 3/075
See application file for complete search history.

(56) References Cited

U.S. PATENT DOCUMENTS

2016/0206748 A1    7/2016 Yousaf
2017/0182220 A1    6/2017 Song et al.
2021/0162092 A1*   6/2021 Pan ...................... C08G 65/331

FOREIGN PATENT DOCUMENTS

CN    106832060    6/2017
CN    107596438    1/2018
(Continued)

OTHER PUBLICATIONS

Chinese Office Action CN Appln. No. 202010455951.3, dated Jul. 20, 2021, 10 page with English Translation.
(Continued)

*Primary Examiner* — Michael F Pepitone
(74) *Attorney, Agent, or Firm* — Fish & Richardson P.C.

(57) ABSTRACT

The present invention provides a polyethylene glycol derivative comprising a repeat unit having the structure of Formula (I) and a terminal group having the structure of Formula (II). The polyethylene glycol derivative provided by the present invention has good biocompatibility, due to the repeat unit
(Continued)

Chemical shift (ppm)

having the structure of Formula (I); and can react with various groups such as amino, (acyl)hydrazino, and aminooxy with a fast reaction rate under mild reaction conditions, due to the o-phthalaldehyde terminal group having the structure of Formula (II). The polyethylene glycol derivative provided by the present invention is mixed with polyethylene glycol having an amino-containing terminal group in an aqueous medium, to rapidly form a chemically cross-linked hydrogel material. The hydrogel material has mild preparation conditions, fast gel-forming speed, high mechanical strength, and good stability. This polyethylene glycol hydrogel can be applied as drug sustained-release carrier, tissue engineering scaffold, etc. in the field of biomedical materials.

10 Claims, 5 Drawing Sheets

(52) U.S. Cl.
CPC .......... *C08J 3/075* (2013.01); *C08G 2650/04* (2013.01); *C08J 2371/02* (2013.01)

(56) References Cited

FOREIGN PATENT DOCUMENTS

| | | | |
|---|---|---|---|
| CN | 108822299 | 11/2018 | |
| CN | 109867822 | 6/2019 | |
| CN | 109939065 | 6/2019 | |
| CN | 110157011 | 8/2019 | |
| WO | WO-2020029432 A1 * | 2/2020 | ............. A61K 47/10 |

OTHER PUBLICATIONS

Chinese Office Action CN Appln. No. 202010455951.3, dated Mar. 9, 2021, 13 page with English Translation.
PCT International Search Report and Written Opinion in International Appln. No. PCT/CN2020/098863, dated Feb. 19, 2021, 14 pages.
Zhang et al., "A Fast and Versatile Cross-Linking Strategy via o-Phthalaldehyde Condenstation for Mechanically Strengthened and Functional Hydrogels", National Science Review, Jun. 2020, 11 pages.
Extended European Search Report in European Appln No. 20938000.5, dated May 4, 2023, 5 pages.

* cited by examiner

Chemical shift (ppm)

POLYETHYLENE GLYCOL DERIVATIVE, PREPARATION METHOD THEREOF, AND POLYETHYLENE GLYCOL HYDROGEL CAPABLE OF PRODUCING A RAPID CROSSLINKING REACTION

CROSS-REFERENCE TO RELATED APPLICATIONS

This application is a U.S. national phase filing under 35 U.S.C. § 371 of International Application No. PCT/CN2020/098863, filed Jun. 29, 2020, which claims priority to Chinese Application No. 202010455951.3, filed May 26, 2020. The entire contents of the prior application are incorporated herein by reference in their entirety.

TECHNICAL FIELD

The present invention falls into the technical field of new biomedical materials, and specifically relates to a polyethylene glycol derivative, a preparation method thereof, and a polyethylene glycol hydrogel capable of producing a rapid crosslinking reaction.

BACKGROUND

Hydrogel is a material with a three-dimensional network structure formed by certain crosslinking. Hydrogel is widely applied in the biomedical field, due to its physical and chemical properties similar to extracellular matrix as well as good biocompatibility.

Polyethylene glycol is a common raw material for preparing hydrogel, including linear polyethylene glycol and multi-arm polyethylene glycol. Due to the low reactivity of the terminal hydroxyl of the polyethylene glycol, it is usually necessary to derivatize polyethylene glycol to produce terminal groups with different functions, such as carboxy, amino, mercapto, and aldehyde groups. Through the chemical reaction of the terminal group, a chemically cross-linked hydrogel can be conveniently prepared, and the hydrogel can also be functionalized by coupling other molecules. The prior art discloses a variety of polyethylene glycol hydrogels, such as polyethylene glycol hydrogel through the reaction of aldehyde group and amino group and polyethylene glycol hydrogel through enzymatic crosslinking reactions. However, the polyethylene glycol hydrogel prepared by the prior art has a slow gel-forming speed, poor stability, low mechanical strength, and the need to add toxic catalysts and other defects that limit its application in the biomedical field.

SUMMARY

In view of above, the technical problem to be solved by the present invention is to provide a polyethylene glycol derivative, a preparation method thereof, and a polyethylene glycol hydrogel capable of producing a rapid crosslinking reaction. The hydrogel prepared from the polyethylene glycol derivative provided by the present invention has the characteristics of mild preparation conditions, fast gel-forming speed, high mechanical strength, etc.

The present invention provides a polyethylene glycol derivative, comprising a repeat unit having the structure of Formula (I) and a terminal group having the structure of Formula (II);

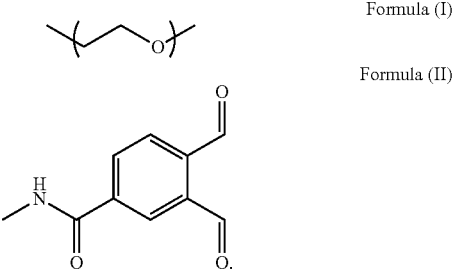

Preferably, the polyethylene glycol derivative has any of the structures of Formula (IIIa), Formula (IIIb), Formula (IIIc), Formula (IIId), and Formula (IIIe):

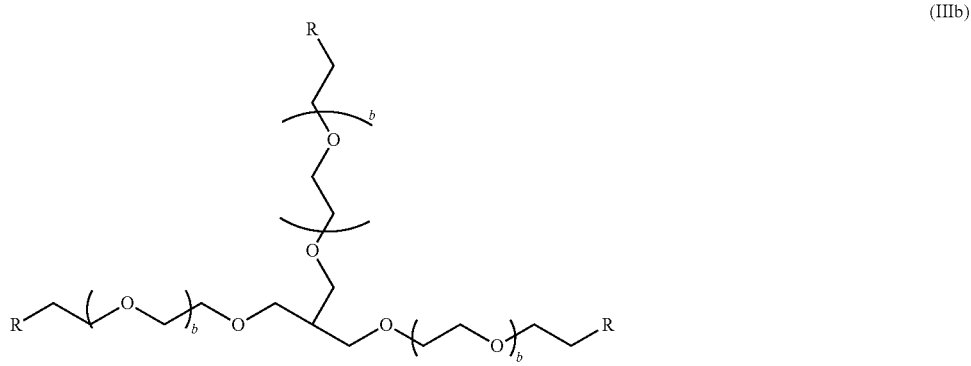

(IIIc)
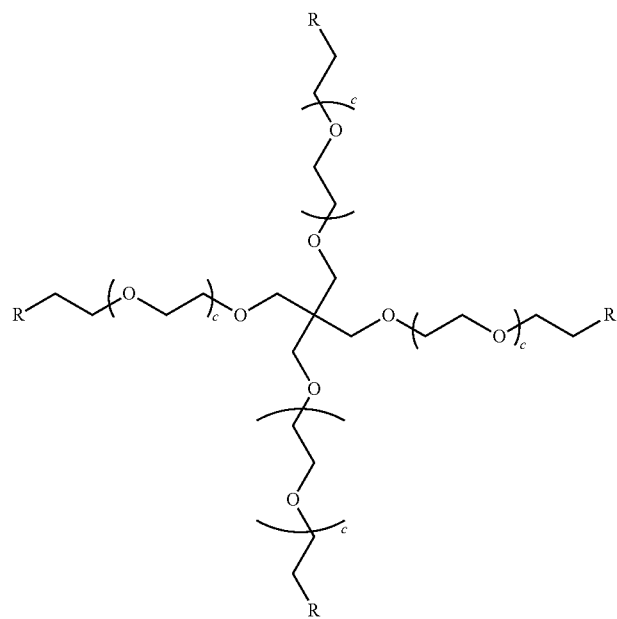
(IIId)
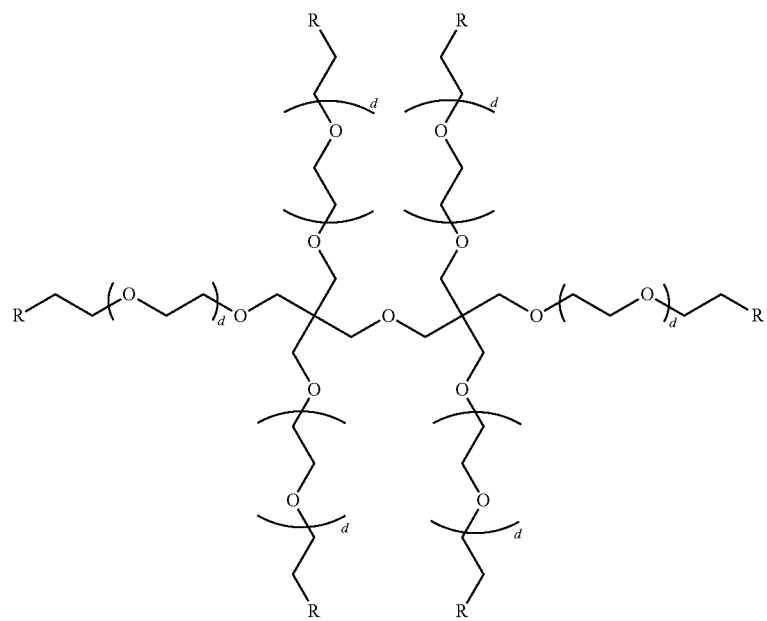

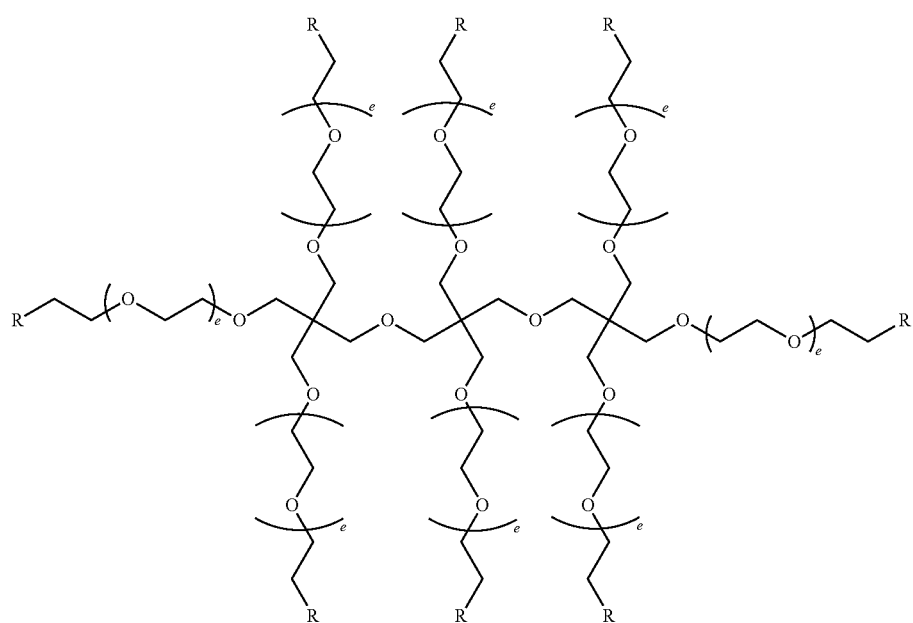

(IIIe)

wherein, a is the degree of polymerization, 1≤a≤1000;
b is the degree of polymerization, 1≤b≤333;
c is the degree of polymerization, 1≤c≤250;
d is the degree of polymerization, 1≤d≤166;
e is the degree of polymerization, 1>e≤125;
R is a terminal group having a structure of Formula (II).

The present invention also provides a preparation method of the above-mentioned polyethylene glycol derivative, comprising the following steps:
A) reacting 1,3-dimethoxy-1,3-dihydroisobenzofuran-5-carboxylic acid succinimidyl ester with polyethylene glycol with amino as terminal group, to obtain a reaction product;
B) deprotecting the reaction product, to obtain a polyethylene glycol derivative.

Preferably, the 1,3-dimethoxy-1,3-dihydroisobenzofuran-5-carboxylic acid succinimidyl ester is prepared according to the following process:
1) brominating 3,4-dimethylbenzoic acid, to prepare 3,4-bis(dibromomethyl)benzoic acid;
2) hydrolyzing 3,4-bis(dibromomethyl)benzoic acid, to obtain 3,4-diformylbenzoic acid;
3) reacting 3,4-diformylbenzoic acid with methanol, to obtain 1,3-dimethoxy-1,3-dihydroisobenzofuran-5-carboxylic acid;
4) reacting 1,3-dimethoxy-1,3-dihydroisobenzofuran-5-carboxylic acid with N-hydroxysuccinimide and a condensation agent, to obtain 1,3-dimethoxy-1,3-dihydroisobenzofuran-5-carboxylic acid succinimidyl ester.

The present invention also provides a polyethylene glycol hydrogel capable of producing a rapid crosslinking reaction, which is formed by connecting a polyethylene glycol derivative and a polyethylene glycol having an amino-containing terminal group via a chemical bond, wherein the polyethylene glycol derivative is the above-mentioned polyethylene glycol derivative.

Preferably, the polyethylene glycol having an amino-containing terminal group comprises a repeat unit having the structure of Formula (IV) and a terminal group having any of the structures of Formula (Va), Formula (Vb), Formula (Vc), Formula (Vd), and Formula (Ve):

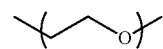

(IV)

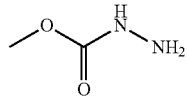

(Va)

(Vb)

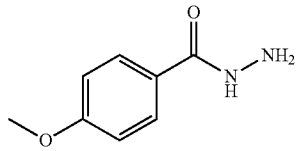

(Vc)

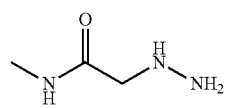

(Vd)

(Ve)

Preferably, the polyethylene glycol having an amino-containing terminal group has any of the structures of Formula (VIa), Formula (VIb), Formula (VIc), Formula (VId), and Formula (VIe):

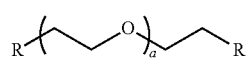 (VIa)
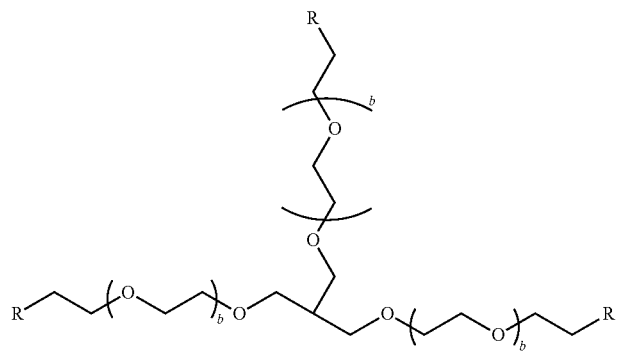 (VIb)
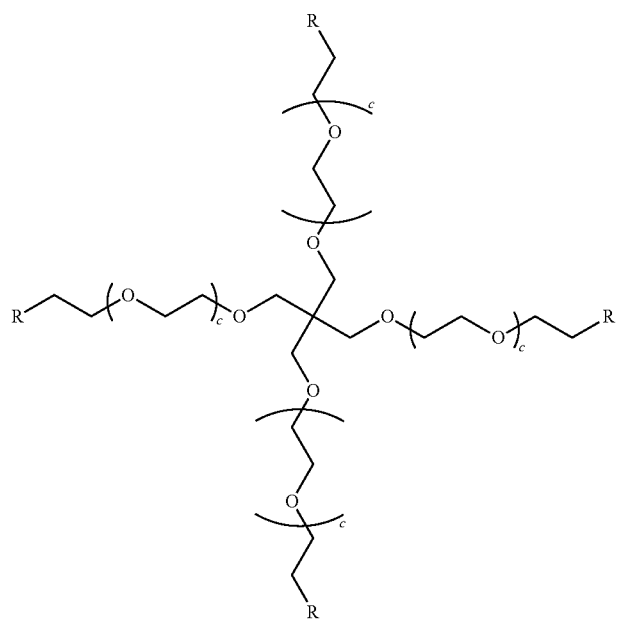 (VIc)
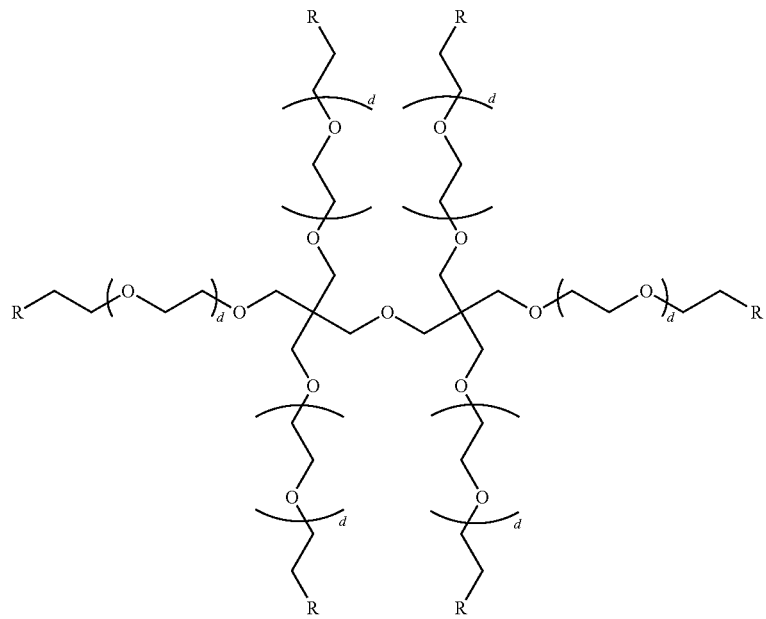 (VId)

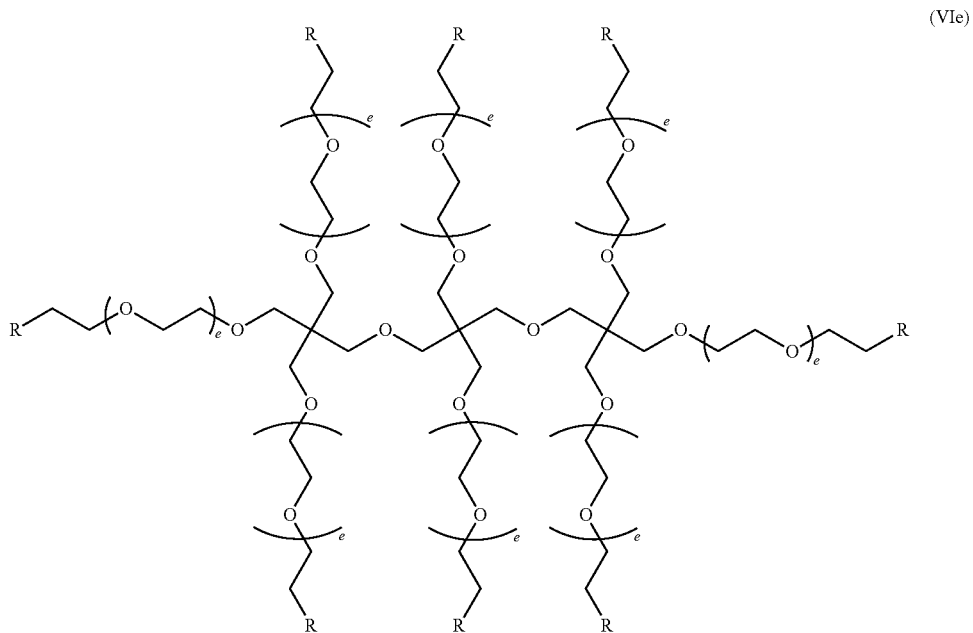

(VIe)

wherein, a is the degree of polymerization, 1≤a≤1000;
b is the degree of polymerization, 1≤b≤333;
c is the degree of polymerization, 1≤c≤250;
d is the degree of polymerization, 1≤d≤166;
e is the degree of polymerization, 1≤e≤125;
R is a terminal group having any of the structures of Formula (Va), Formula (Vb), Formula (Vc), Formula (Vd), and Formula (Ve).

The present invention also provides a preparation method of the above-mentioned polyethylene glycol hydrogel, which is prepared from polyethylene glycol derivative, polyethylene glycol having an amino-containing terminal group, and solvent.

Preferably, the solvent is water, physiological saline, or buffer solution;
the polyethylene glycol derivative has a mass-volume concentration of 1~1000 mg/mL; and
the polyethylene glycol having an amino-containing terminal group has a mass-volume concentration of 1~1000 mg/mL.

Preferably, the mass ratio of the polyethylene glycol derivative to the polyethylene glycol having an amino-containing terminal group is 1:0.01~100.

Compared with the prior art, the present invention provides a polyethylene glycol derivative comprising a repeat unit having the structure of Formula (I) and a terminal group having the structure of Formula (II). The polyethylene glycol derivative provided by the present invention has a good biocompatibility, due to the repeat unit having the structure of Formula (I); and can react with various groups such as amino, (acyl)hydrazino, and aminooxy with a fast reaction rate and under mild reaction conditions, due to the o-phthalaldehyde terminal group having the structure of Formula (II). The polyethylene glycol derivative provided by the present invention is mixed with polyethylene glycol having an amino-containing terminal group in an aqueous medium, to rapidly form a chemically cross-linked hydrogel material. The hydrogel material has mild preparation conditions, fast gel-forming speed, high mechanical strength, and good stability. This polyethylene glycol hydrogel can be applied as a sustained-release drug carrier, a tissue engineering scaffold, etc. in the field of biomedical materials.

DESCRIPTION OF EMBODIMENTS

Figure 1:
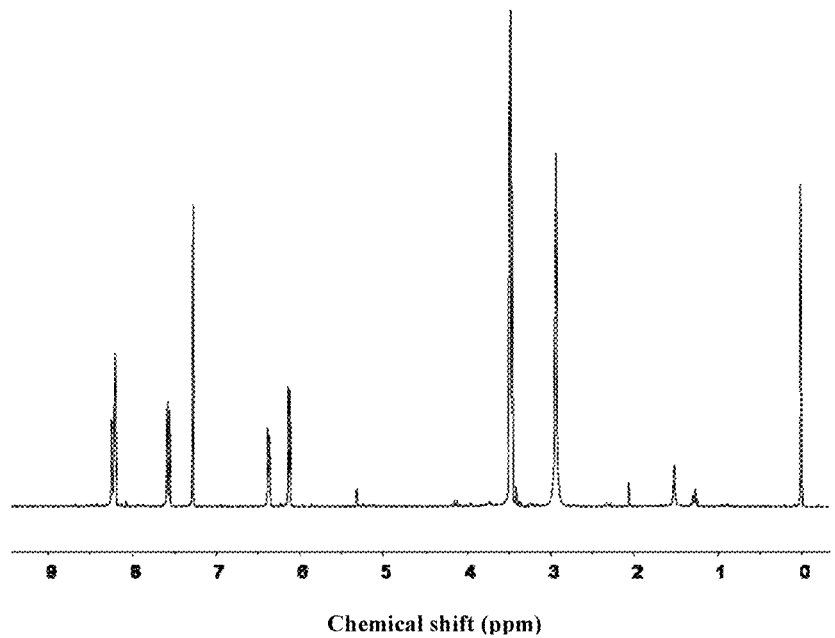
FIG. 1 shows the H-NMR spectrum of 1,3-dimethoxy-1,3-dihydroisobenzofuran-5-carboxylic acid succinimidyl ester as prepared in Example 4 of the present invention.

The present invention provides a polyethylene glycol derivative, comprising a repeat unit having the structure of Formula (I) and a terminal group having the structure of Formula (II):

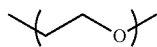

Formula (I)

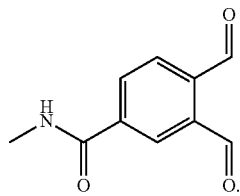

Formula (II)

In the present invention, the polyethylene glycol derivative may be a linear polyethylene glycol derivative or a multi-arm polyethylene glycol derivative.

In some specific embodiments of the present invention, the polyethylene glycol derivative has any of the structures of Formula (IIIa), Formula (IIIb), Formula (IIIc), Formula (IIId), and Formula (IIIe):

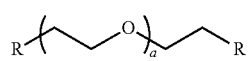

(IIIa)

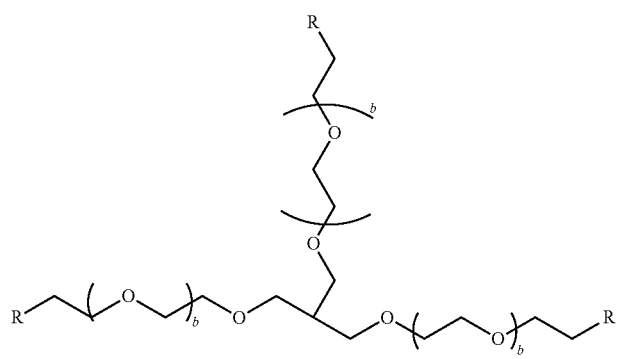

(IIIb)

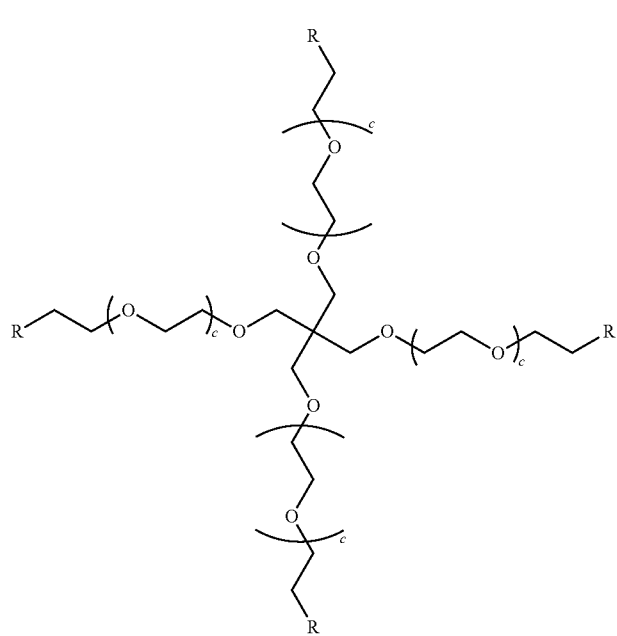

(IIIc)

-continued

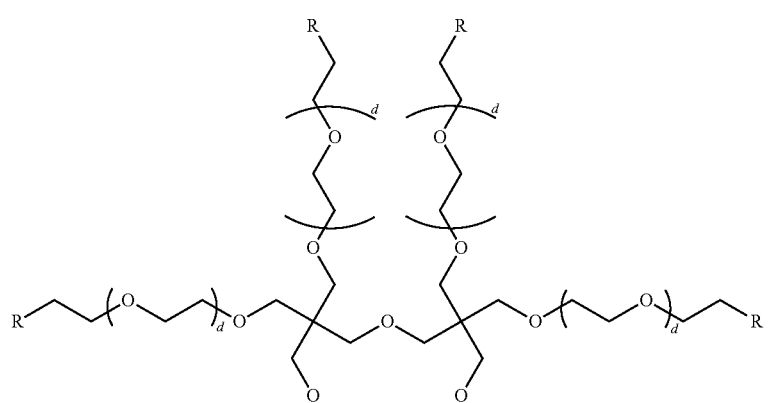
(IIId)

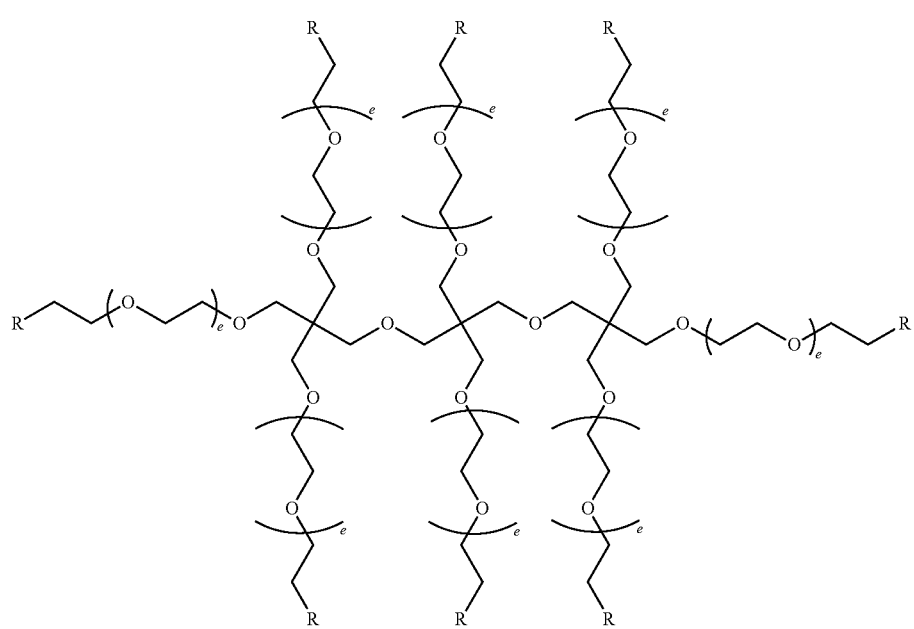
(IIIe)

wherein, a is the degree of polymerization, 1≤a≤1000;
b is the degree of polymerization, 1≤b≤333;
c is the degree of polymerization, 1≤c≤250;
d is the degree of polymerization, 1≤d≤166;
e is the degree of polymerization, 1≤e≤125;
R is a terminal group having the structure of Formula (II).

The present invention also provides a preparation method of the above polyethylene glycol derivative, which comprises the following steps:

A) reacting 1,3-dimethoxy-1,3-dihydroisobenzofuran-5-carboxylic acid succinimidyl ester with polyethylene glycol having amino as terminal group, to obtain a reaction product;
B) deprotecting the reaction product, to obtain a polyethylene glycol derivative.

The reaction process is as follows:

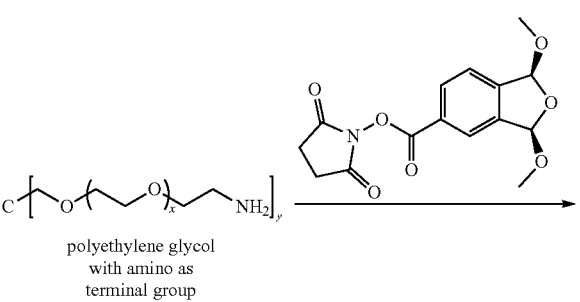

polyethylene glycol
with amino as
terminal group

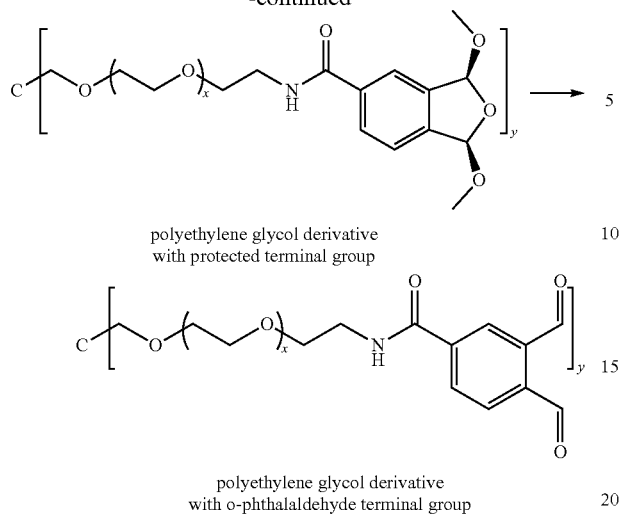

polyethylene glycol derivative
with protected terminal group polyethylene glycol derivative
with o-phthalaldehyde terminal group In the present invention, 1,3-dimethoxy-1,3-dihydroisobenzofuran-5-carboxylic acid succinimidyl ester and polyethylene glycol with amino as terminal group are dissolved in an organic solvent, reacted in the presence of acid-binding agent, and settled, to obtain the reaction product.

The molar equivalent of 1,3-dimethoxy-1,3-dihydroisobenzofuran-5-carboxylic acid succinimidyl ester is 1.2~5 times, preferably 2 times, of that of the amino group in the polyethylene glycol with amino as terminal group; the organic solvent is preferably anhydrous dichloromethane; and the acid-binding agent is preferably anhydrous pyridine.

The reaction time is 24~72 h, preferably 48 h; and the reaction temperature is 10~40° C., preferably 25° C.

In the present invention, anhydrous ethyl ether is preferably used for the settling; and the settled solid is filtered, and dried in vacuum, to obtain the reaction product.

In the present invention, after the reaction product is obtained, the reaction product is deprotected, dialyzed, and lyophilized, to obtain a polyethylene glycol derivative.

The deprotection can adopt a technical solution well known to those skilled in the art. In the present invention, a mixed solvent of trifluoroacetic acid and water is preferably used; the volume of the mixed solvent is 5~20 times, preferably 5 times, of the mass of the reaction product; the deprotection time is 0.5~3 h, preferably 1 h; and the deprotection temperature is 10~40° C., preferably 25° C.

The dialysis and lyophilization can adopt the technical solutions well known to those skilled in the art.

In the present invention, the 1,3-dimethoxy-1,3-dihydroisobenzofuran-5-carboxylic acid succinimidyl ester is prepared according to the following process:
1) brominating 3,4-dimethylbenzoic acid, to prepare 3,4-bis(dibromomethyl)benzoic acid;
2) hydrolyzing 3,4-bis(dibromomethyl)benzoic acid, to obtain 3,4-diformylbenzoic acid;
3) reacting 3,4-diformylbenzoic acid with methanol, to obtain 1,3-dimethoxy-1,3-dihydroisobenzofuran-5-carboxylic acid; and
4) reacting 1,3-dimethoxy-1,3-dihydroisobenzofuran-5-carboxylic acid with N-hydroxysuccinimide and a condensation agent, to obtain 1,3-dimethoxy-1,3-dihydroisobenzofuran-5-carboxylic acid succinimidyl ester.

The reaction process is as follows:

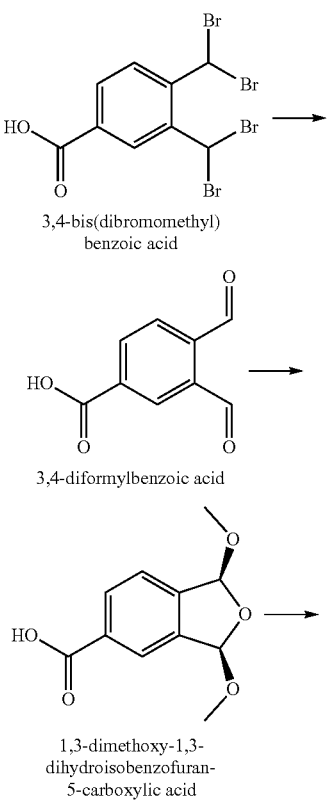

3,4-dimethylbenzoic acid 3,4-bis(dibromomethyl)
benzoic acid 3,4-diformylbenzoic acid 1,3-dimethoxy-1,3-
dihydroisobenzofuran-
5-carboxylic acid 1,3-dimethoxy-1,3-dihydroisobenzofuran-5-carboxylic
acid succinimide ester Specifically, in the present invention, 3,4-dimethylbenzoic acid is brominatd, to prepare 3,4-bis(dibromomethyl) benzoic acid.

The bromination reaction can adopt a technical solution well known to those skilled in the art. The present invention uses N-bromosuccinimide as brominating agent, any one of benzoyl peroxide and azobisisobutyronitrile as free radical initiator, and carbon tetrachloride as solvent, for the bromination reaction.

The molar equivalent of N-bromosuccinimide is 3~5 times, preferably 4 times, of that of 3,4-dimethylbenzoic acid; the molar equivalent of benzoyl peroxide is 0.05~0.5 times, preferably 0.1 times, of that of 3,4-dimethylbenzoic acid; and the volume (ml) of carbon tetrachloride is 10~50 times, preferably 20 times, of the mass (g) of 3,4-dimethylbenzoic acid.

The bromination reaction temperature is 70~90° C., preferably 81° C.; and the bromination reaction time is 10~20 h, preferably 15 h.

After the bromination reaction is completed, the reaction mixture is filtered; the filter cake is washed with benzene or ethyl ether; all the filtrates are combined and concentrated, and then vacuum dried; and the solid product is recrystallized in acetonitrile, to obtain 3,4-bis(dibromomethyl)benzoic acid.

In the present invention, a rotary evaporator is preferably used for concentration; the concentration temperature is preferably 30° C.; and it is preferable to be concentrated to 10% of the liquid volume.

The recrystallization can adopt a technical solution well known to those skilled in the art.

In the present invention, 3,4-bis(dibromomethyl)benzoic acid is subjected to hydrolysis reaction, to obtain 3,4-diformylbenzoic acid.

The hydrolysis reaction can adopt the technical solutions well known to those skilled in the art. In the present invention, 3,4-bis(dibromomethyl)benzoic acid is preferably dissolved in an aqueous solution of sodium carbonate for the hydrolysis reaction.

The mass-volume concentration of the aqueous solution of sodium carbonate is 10%; the volume of the aqueous solution of sodium carbonate is 5-20 times, preferably 10 times, of the mass of 3,4-bis(dibromomethyl)benzoic acid.

The hydrolysis reaction temperature is 60~80° C., preferably 70° C.; and the hydrolysis reaction time is 3-5 h, preferably 4 h.

After the hydrolysis reaction is completed, the pH of the reaction solution is adjusted to 0-3, preferably 1, with concentrated hydrochloric acid; extracted by ethyl acetate; concentrated, and vacuum dried, to obtain 3,4-diformylbenzoic acid.

In the present invention, 3,4-diformylbenzoic acid, methanol, and a catalyst are reacted to obtain 1,3-dimethoxy-1,3-dihydroisobenzofuran-5-carboxylic acid.

The catalyst is preferably scandium trifluoromethanesulfonate; the reaction temperature is 10~40° C., preferably 25° C.; and the reaction time is 6~24 h, preferably 12 h.

In the present invention, 1,3-dimethoxy-1,3-dihydroisobenzofuran-5-carboxylic acid is reacted with N-hydroxysuccinimide and a condensation agent in an organic solvent, to obtain 1,3-dimethoxy-1,3-dihydroisobenzofuran-5-carboxylic acid succinimidyl ester.

The condensation agent is any of dicyclohexylcarbodiimide, 1-(3-dimethylaminopropyl)-3-ethylcarbodiimide hydrochloride, and diisopropylcarbodiimide, preferably 1-(3-dimethylaminopropyl)-3-ethylcarbodiimide hydrochloride; and the organic solvent is any one of dimethylformamide, dimethyl sulfoxide, and acetonitrile, preferably acetonitrile.

The reaction temperature is 10~40° C., preferably 25° C.; and the reaction time is 6~24 h, preferably 12 h.

After the reaction is completed, the crude product is purified by silica gel column chromatography, to obtain 1,3-dimethoxy-1,3-dihydroisobenzofuran-5-carboxylic acid succinimidyl ester. The mobile phase of the column chromatography is preferably n-hexane and ethyl acetate at a volume ratio of 1:5~1:1, preferably 1:3.

The present invention also provides a polyethylene glycol hydrogel capable of producing a rapid crosslinking reaction, formed by connecting a polyethylene glycol derivative and a polyethylene glycol having an amino-containing terminal group via a chemical bond, wherein the polyethylene glycol derivative is the above-mentioned polyethylene glycol derivative.

Herein, the polyethylene glycol having an amino-containing terminal group comprises a repeat unit having the structure of Formula (IV) and a terminal group having any one of the structures of Formula (Va), Formula (Vb), Formula (Vc), Formula (Vd), and Formula (Ve);

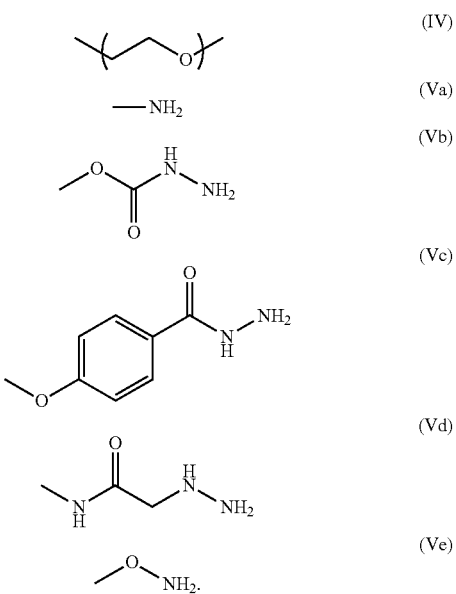

The polyethylene glycol having an amino-containing terminal group may be a linear polyethylene glycol having an amino-containing terminal group or a multi-arm polyethylene glycol having an amino-containing terminal group.

In some specific embodiments of the present invention, the polyethylene glycol having an amino-containing terminal group has any one of the structures of Formula (VIa), Formula (VIb), Formula (VIc), Formula (VId), and Formula (VIe):

(VIa)

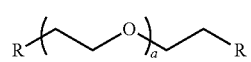

(VIb)
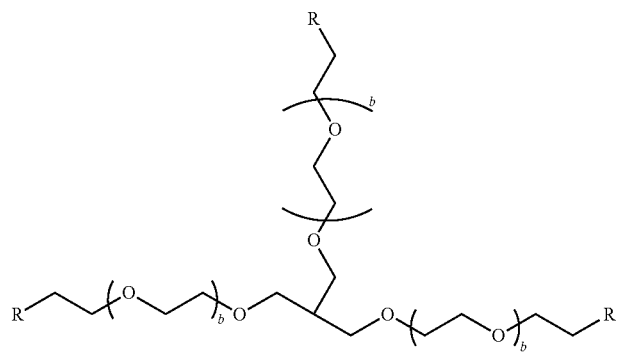
(VIc)
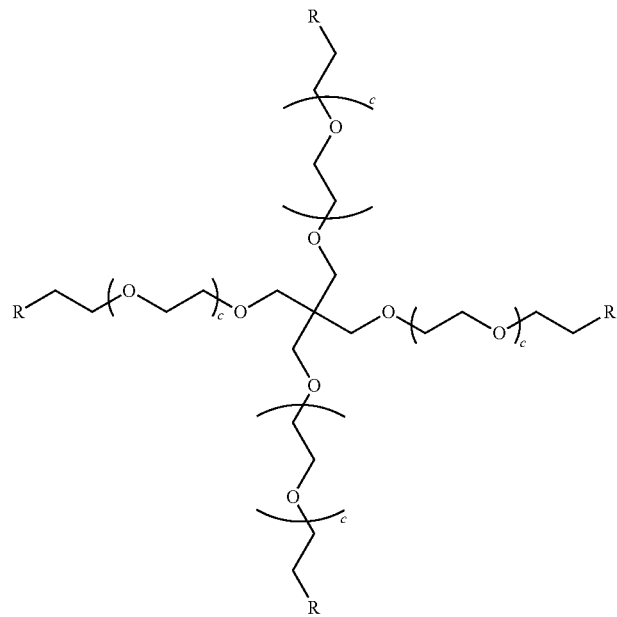
(VId)
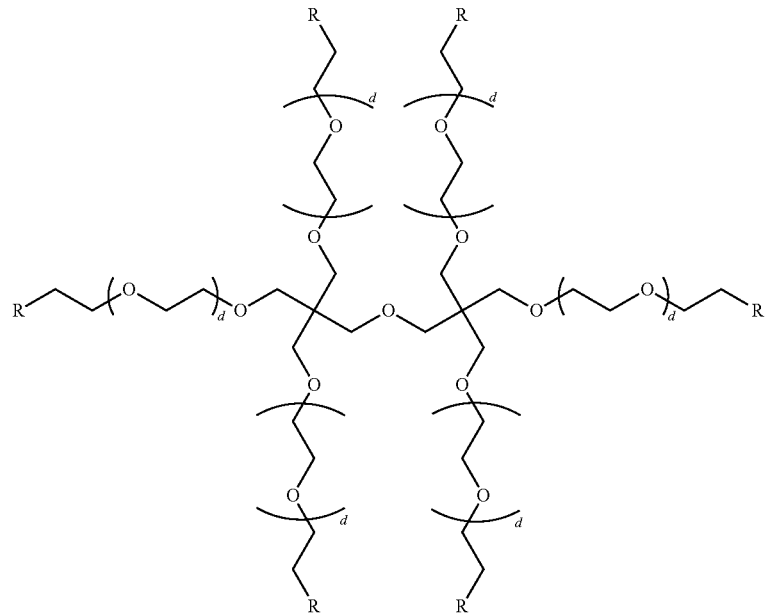

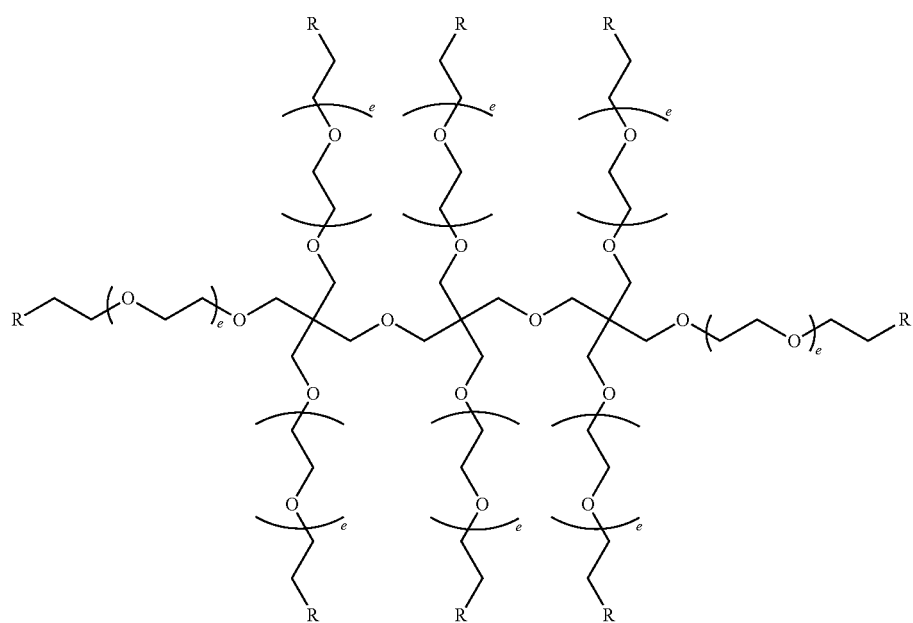

(VIe)

wherein, a is the degree of polymerization, 1≤a≤1000;
b is the degree of polymerization, 1≤b≤333;
c is the degree of polymerization, 1≤c≤250;
d is the degree of polymerization, 1≤d≤166;
e is the degree of polymerization, 1≤e≤125;
R is a terminal group having any of the structures of Formula (Va), Formula (Vb), Formula (Vc), Formula (Vd), and Formula (Ve).

The present invention also provides a preparation method of the above-mentioned polyethylene glycol hydrogel, which is prepared from a polyethylene glycol derivative, a polyethylene glycol having an amino-containing terminal group, and a solvent.

In the present invention, the preparation process of the polyethylene glycol hydrogel includes:
(1) preparing solution 1 of polyethylene glycol derivative;
(2) preparing solution 2 of polyethylene glycol having an amino-containing terminal group;
(3) mixing the solution 1 and the solution 2, to obtain a polyethylene glycol hydrogel via a chemical reaction.

In the solution 1, the mass-volume concentration of the polyethylene glycol derivative is 1~1000 mg/mL, preferably 10~200 mg/mL.

In the solution 2, the mass-volume concentration of the polyethylene glycol having an amino-containing terminal group is 1~1000 mg/mL, preferably 10~200 mg/mL.

The solvent used in the preparation of solution 1 and solution 2 is selected from water, physiological saline, or buffer solution, and the buffer solution is selected from phosphate buffer solution.

The mass ratio of the polyethylene glycol derivative to the polyethylene glycol having an amino-containing terminal group is 1:0.01~100, preferably 1:0.1~10.

The polyethylene glycol derivative provided by the present invention has a good water-solubility and biocompatibility, and the o-phthalaldehyde at terminal can chemically react with various groups.

The polyethylene glycol derivative provided by the present invention comprises a main chain of polyethylene glycol and a terminal group of o-phthalaldehyde. The polyethylene glycol hydrogel is formed by connecting the above-mentioned polyethylene glycol derivative and polyethylene glycol having an amino-containing terminal group via a chemical bond. The polyethylene glycol hydrogel of the present invention has a fast gel-forming speed, high mechanical strength, excellent tissue adhesion ability, and good biocompatibility. The polyethylene glycol hydrogel of the present invention has potential applications in the following fields: drug sustained-release carriers, tissue engineering scaffolds, and hemostatic sealing coatings.

In order to further understand the present invention, the polyethylene glycol derivative, the preparation method thereof, and the polyethylene glycol hydrogel capable of producing a rapid crosslinking reaction as provided in the present invention will be illustrated below in conjugation with Examples, but the protection scope of the present invention is not limited by the following Examples. Unless otherwise specified, the reagents used in the following Examples are purchased from J&K Chemical, and the solvents used are purchased from Beijing Chemical Plant.

Example 1

3,4-dimethylbenzoic acid (12 g) and N-bromosuccinimide (57 g) were dissolved in hot carbon tetrachloride (200 mL), and then 1.6 g of benzoyl peroxide was slowly added. The mixture was refluxed for reaction at 81° C. for 15 h. After filtration, the filter cake was washed with benzene (200 mL) and ethyl ether (300 mL). All the filtrates were combined, concentrated by a rotary evaporator to a remaining liquid volume of 70 mL, and then evacuated to solid by a vacuum pump. The obtained solid was recrystallized in acetonitrile, to obtain 3,4-bis(dibromomethyl)benzoic acid (13 g, 35%).

Example 2

3,4-bis(dibromomethyl)benzoic acid (13 g) prepared in Example 1 was dissolved in an aqueous sodium carbonate solution (130 mL) with a mass-volume concentration of 10%, and reacted at 70° C. for 4 h. The pH of the reaction solution was adjusted to 1 with concentrated hydrochloric acid, and then extracted with ethyl acetate (4×60 mL). The organic phases were combined, washed with saturated brine, dried over anhydrous sodium sulfate, filtered, and vacuum dried, to obtain 3,4-diformylbenzoic acid (2.8 g, 56%).

Example 3

3,4-bis(dibromomethyl)benzoic acid (2.8 g) prepared in Example 2 was dissolved in anhydrous methanol (60 mL), followed by the addition of the catalyst scandium trifluoromethanesulfonate (420 mg), and the reaction was conducted for 12 h. After vacuum drying, 1,3-dimethoxy-1,3-dihydroisobenzofuran-5-carboxylic acid (3.5 g, 100%) was obtained.

Example 4

1,3-dimethoxy-1,3-dihydroisobenzofuran-5-carboxylic acid prepared in Example 4 and N-hydroxysuccinimide (3.6 g) were dissolved in anhydrous acetonitrile (80 mL), followed by the addition of 1-(3-dimethylaminopropyl)-3-ethylcarbodiimide hydrochloride (4.5 g), and the reaction was conducted for 12 h. Most of the solvent was removed by rotary evaporation, and the remaining mixture was dissolved in dichloromethane, washed with saturated brine for 3 times, and dried over anhydrous magnesium sulfate. The crude product was purified by silica gel column chromatography, to obtain 1,3-dimethoxy-1,3-dihydroisobenzofuran-5-carboxylic acid succinimidyl ester (2.3 g, 45%), wherein the mobile phase is n-hexane and ethyl acetate at a volume ratio of 1:3. Referring to FIG. 1, FIG. 1 shows the H-NMR spectrum of 1,3-dimethoxy-1,3-dihydroisobenzofuran-5-carboxylic acid succinimidyl ester as prepared in Example 4 of the present invention.

Example 5

The linear polyethylene glycol with amino as terminal group (number-average molecular weight: 2000, 2.0 g) was dissolved in 25 mL of dichloromethane, and 1 mL of pyridine was added as acid-binding agent, followed by the dropwise addition of a solution (25 mL) of 1,3-dimethoxy-1,3-dihydroisobenzofuran-5-carboxylic acid succinimidyl ester prepared in Example 4 (1.3 g) in dichloromethane, and the reaction was conducted for 48 h. The reaction solution was poured into 500 mL of glacial ethyl ether, settled, filtered, and dried in vacuum, to obtain a linear polyethylene glycol derivative with protected terminal group (1.9 g, 95%).

The linear polyethylene glycol derivative with protected terminal group (1.9 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 500 and dialyzed for 48 h, then lyophilized, to obtain a linear polyethylene glycol derivative (1.6 g, 84%).

Example 6

Three-arm polyethylene glycol with amino as terminal group (number-average molecular weight: 10000, 2.0 g) was dissolved in 25 mL of dichloromethane, and 1 mL of pyridine was added as acid-binding agent, followed by the dropwise addition of a solution (25 mL) of 1,3-dimethoxy-1,3-dihydroisobenzofuran-5-carboxylic acid succinimidyl ester (0.39 g) in dichloromethane, and the reaction was conducted for 48 h. The reaction solution was poured into 500 mL of glacial ethyl ether, settled, filtered, and dried in vacuum, to obtain a three-arm polyethylene glycol derivative with protected terminal group (2.0 g, 100%).

The three-arm polyethylene glycol derivative with protected terminal group (2.0 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 3500 and dialyzed for 48 h, then lyophilized, to obtain a three-arm polyethylene glycol derivative (1.8 g, 90%).

Example 7

Figure 2:
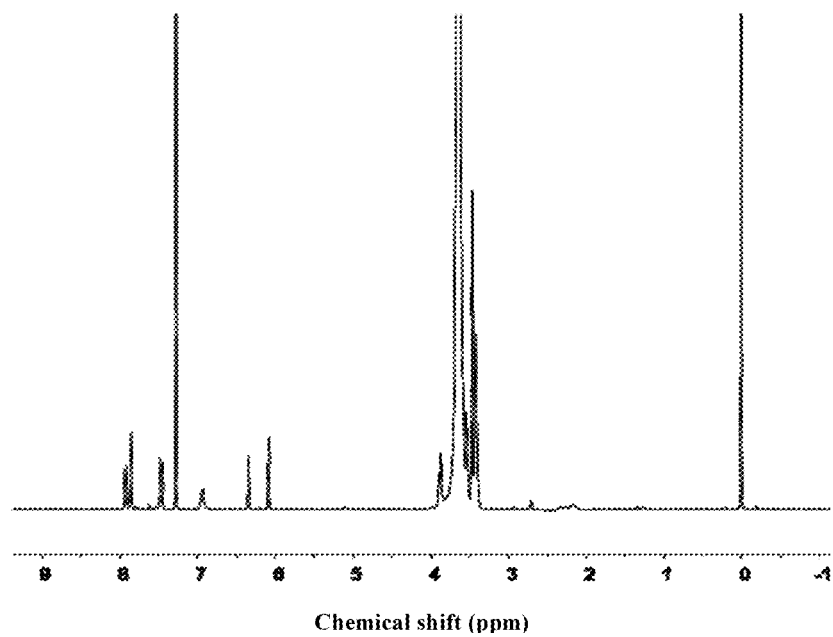
FIG. 2 shows the H-NMR spectrum of the four-arm polyethylene glycol derivative with protected terminal group as prepared in Example 7 of the present invention.

Four-arm polyethylene glycol with amino as terminal group (number-average molecular weight: 10000, 2.0 g) was dissolved in 25 mL of dichloromethane, and 1 mL of pyridine was added as acid-binding agent, followed by the dropwise addition of a solution (25 mL) of 1,3-dimethoxy-1,3-dihydroisobenzofuran-5-carboxylic acid succinimidyl ester (0.51 g) in dichloromethane, and the reaction was conducted for 48 h. The reaction solution was poured into 500 mL of glacial ethyl ether, settled, filtered, and dried in vacuum, to obtain a four-arm polyethylene glycol derivative with protected terminal group (2.0 g, 100%). Referring to FIG. 2, FIG. 2 shows the H-NMR spectrum of the four-arm polyethylene glycol derivative with protected terminal group as prepared in Example 7 of the present invention.

Figure 3:
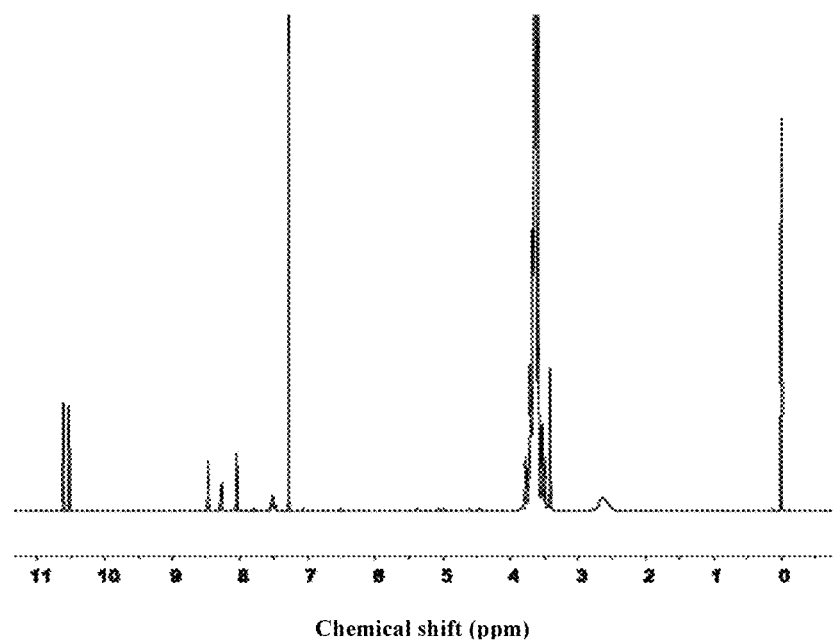
FIG. 3 shows the H-NMR spectrum of the four-arm polyethylene glycol derivative as prepared in Example 7 of the present invention.

The four-arm polyethylene glycol derivative with protected terminal group (2.0 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 3500 and dialyzed for 48 h, then lyophilized, to obtain a four-arm polyethylene glycol derivative (1.9 g, 95%). Referring to FIG. 3, FIG. 3 shows the H-NMR spectrum of the four-arm polyethylene glycol derivative as prepared in Example 7 of the present invention.

Example 8

Four-arm polyethylene glycol with amino as terminal group (number-average molecular weight: 20000, 2.0 g) was dissolved in 25 mL of dichloromethane, 1 mL of pyridine was added as acid-binding agent, followed by the dropwise addition of a solution (25 mL) of 1,3-dimethoxy-1,3-dihydroisobenzofuran-5-carboxylic acid succinimidyl ester (0.26 g) in dichloromethane, and the reaction was conducted for 48 h. The reaction solution was poured into 500 mL of glacial ethyl ether, settled, filtered, and dried in vacuum, to obtain a four-arm polyethylene glycol derivative with protected terminal group (1.9 g, 95%).

The four-arm polyethylene glycol derivative with protected terminal group (1.9 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 7000 and dialyzed for 48 h, then lyophilized, to obtain a four-arm polyethylene glycol derivative (1.8 g, 95%).

Example 9

Six-arm polyethylene glycol with amino as terminal group (number-average molecular weight: 10000, 2.0 g) was dissolved in 25 mL of dichloromethane, and 1 mL of pyridine was added as acid-binding agent, followed by the dropwise addition of a solution (25 mL) of 1,3-dimethoxy-1,3-dihydroisobenzofuran-5-carboxylic acid succinimidyl ester (0.77 g) in dichloromethane, and the reaction was conducted for 48 h. The reaction solution was poured into 500 mL of glacial ethyl ether, settled, filtered, and dried in vacuum, to obtain a six-arm polyethylene glycol derivative with protected terminal group (2.0 g, 100%).

The six-arm polyethylene glycol derivative with protected terminal group (2.0 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 3500 and dialyzed for 48 h, then lyophilized, to obtain a six-arm polyethylene glycol derivative (1.8 g, 90%).

Example 10

Eight-arm polyethylene glycol with amino as terminal group (number-average molecular weight: 10000, 2.0 g) was dissolved in 25 mL of dichloromethane, and 1 mL of pyridine was added as acid-binding agent, followed by the dropwise addition of a solution (25 mL) of 1,3-dimethoxy-1,3-dihydroisobenzofuran-5-carboxylic acid succinimidyl ester (1.0 g) in dichloromethane, and the reaction was conducted for 48 h. The reaction solution was poured into 500 mL of glacial ethyl ether, settled, filtered, and dried in vacuum, to obtain an eight-arm polyethylene glycol derivative with protected terminal group (2.0 g, 100%).

The eight-arm polyethylene glycol derivative with protected terminal group (2.0 g) was dissolved in 5 mL of water, and then 5 mL of trifluoroacetic acid was added dropwise. After the reaction under stirring for 1 h, it was diluted with water to 50 mL, transferred to a dialysis bag with a molecular weight cut-off of 3500 and dialyzed for 48 h, then lyophilized, to obtain an eight-arm polyethylene glycol derivative (1.9 g, 95%).

Example 11

The four-arm polyethylene glycol derivative prepared in Example 7 (number-average molecular weight: 10000, 60 mg) was weighed and dissolved in PBS (1 mL) to obtain solution 1. The four-arm polyethylene glycol with amino as terminal group (as shown by Formula Va) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the gel-forming time is 40 seconds.

Figure 4:
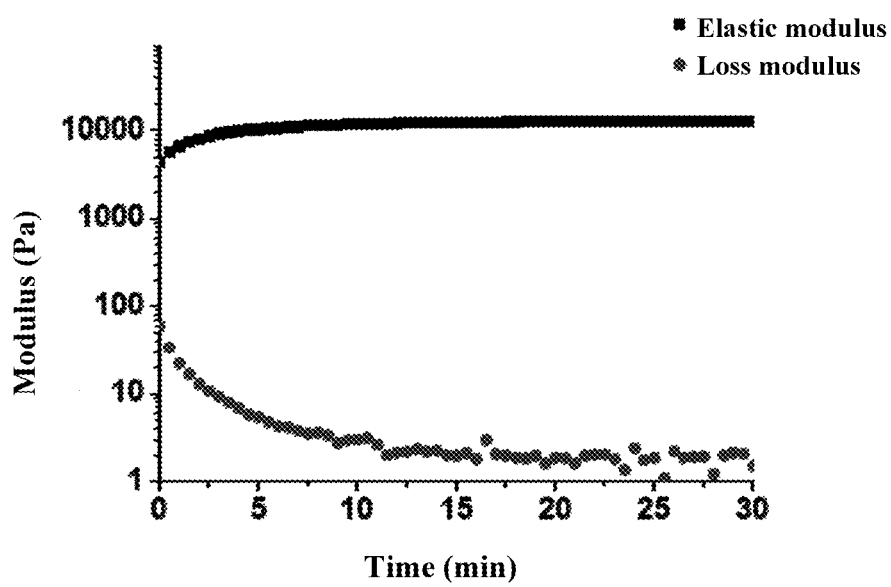
FIG. 4 shows the changes of storage modulus and loss modulus for the mixed solution as prepared in Example 11 of the present invention over time.

The solution 1 (150 μL) and the solution 2 (150 μL) were mixed thoroughly, and then quickly transferred to a rheometer to measure the changes over time of elastic modulus and loss modulus for the mixed solution, wherein the elastic modulus of the hydrogel is 13.0 kPa. Referring to FIG. 4, FIG. 4 shows the rheological test chart of the polyethylene glycol hydrogel prepared in Example 11 of the present invention. The elastic modulus quickly exceeds the loss modulus, indicating that the solution quickly transforms into a hydrogel. After complete crosslinking, the elastic modulus of the hydrogel is 13.0 kPa.

Example 12

The four-arm polyethylene glycol derivative prepared in Example 7 (number-average molecular weight: 10000, 60 mg) was weighed and dissolved in PBS (1 mL) to obtain solution 1. The four-arm polyethylene glycol with carbazate as terminal group (as shown by Formula Vb) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the gel-forming time is 290 seconds.

Figure 5:
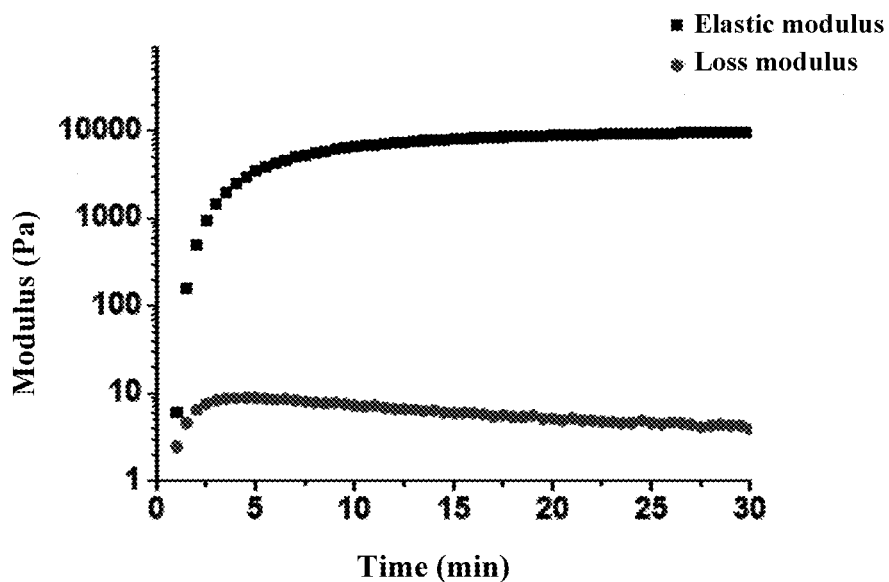
FIG. 5 shows the changes of storage modulus and loss modulus for the mixed solution as prepared in Example 12 of the present invention over time.

The solution 1 (150 μL) and the solution 2 (150 μL) were mixed thoroughly, and then quickly transferred to a rheometer to measure the changes over time of storage modulus and loss modulus for the mixed solution, wherein the elastic modulus of the hydrogel is 11.1 kPa. Referring to FIG. 5, FIG. 5 shows the rheological test chart of the polyethylene glycol hydrogel prepared in Example 12 of the present invention. The elastic modulus quickly exceeds the loss modulus, indicating that the solution quickly transforms into a hydrogel. After complete crosslinking, the elastic modulus of the hydrogel is 11.1 kPa.

Example 13

The four-arm polyethylene glycol derivative prepared in Example 7 (number-average molecular weight: 10000, 60 mg) was weighed and dissolved in PBS (1 mL) to obtain solution 1. The four-arm polyethylene glycol with aminooxy as terminal group (as shown by Formula Ve) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the gel-forming time is 160 seconds.

Figure 6:
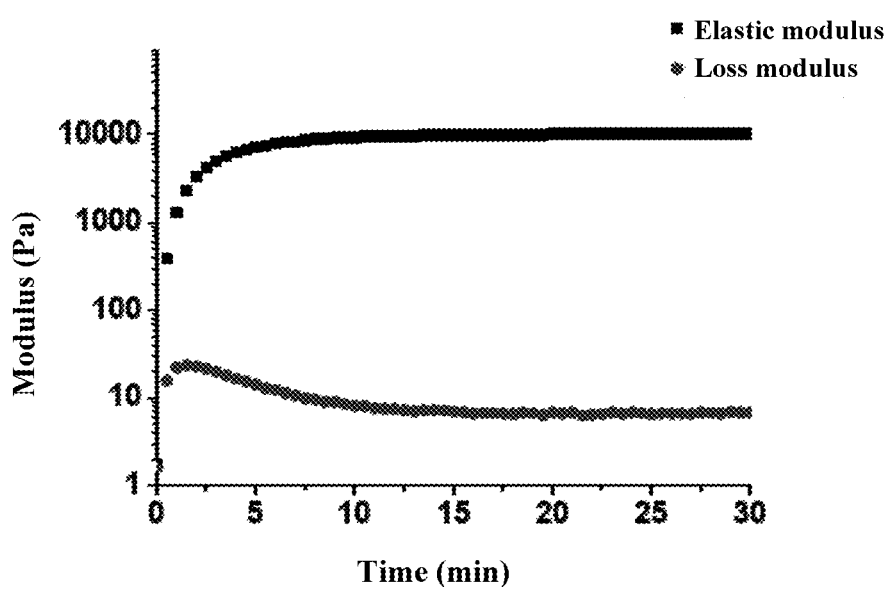
FIG. 6 shows the changes of storage modulus and loss modulus for the mixed solution as prepared in Example 13 of the present invention over time.

The solution 1 (150 μL) and the solution 2 (150 μL) were mixed thoroughly, and then quickly transferred to a rheometer to measure the changes over time of storage modulus and loss modulus for the mixed solution, wherein the elastic modulus of the hydrogel is 10.6 kPa. Referring to FIG. 6, FIG. 6 shows the rheological test chart of the polyethylene glycol hydrogel prepared in Example 13 of the present invention. The elastic modulus quickly exceeds the loss modulus, indicating that the solution quickly transforms into a hydrogel. After complete crosslinking, the elastic modulus of the hydrogel is 10.6 kPa.

Example 14

The four-arm polyethylene glycol derivative prepared in Example 7 (number-average molecular weight: 10000, 90 mg) was weighed and dissolved in PBS (1 mL) to obtain solution 1. The four-arm polyethylene glycol with amino as terminal group (as shown by Formula Va) (number-average molecular weight: 10000, 90 mg) was weighed and dissolved in PBS (1 mL) to obtain solution 2. Each barrel in the double-barreled syringe was used to draw one solution respectively, and the solutions were simultaneously injected to obtain a hydrogel.

Figure 7:
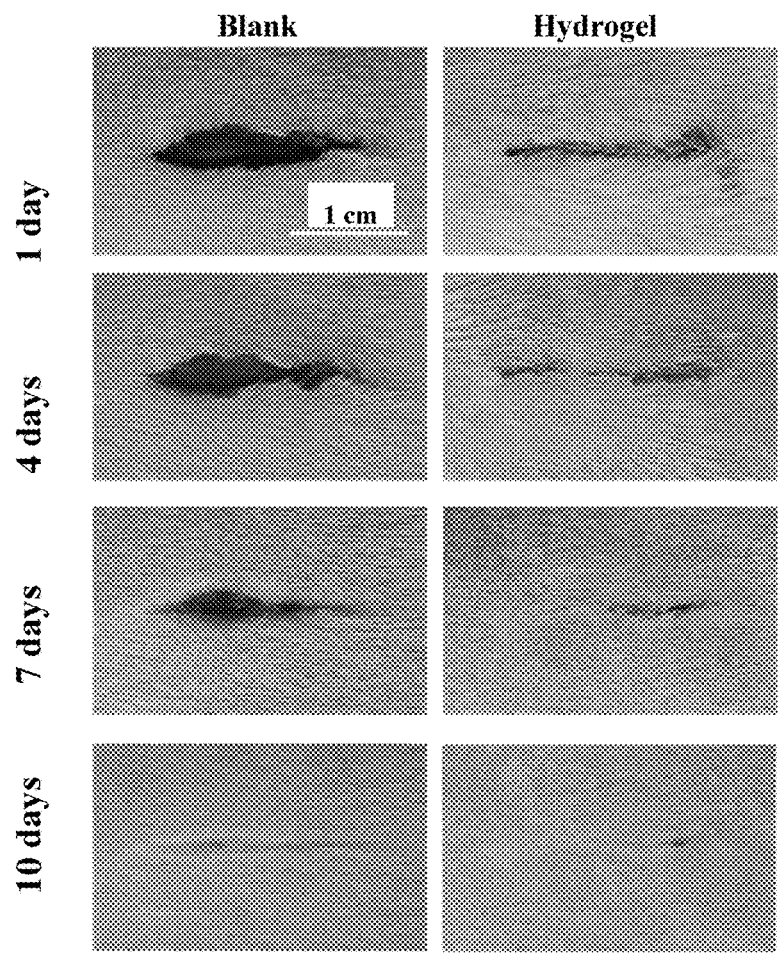
FIG. 7 shows the use of the polyethylene glycol hydrogel as prepared in Example 14 of the present invention in the wound closure of rat skin.

The hydrogel prepared in this Example, which was applied to a wound (2 cm) on the back of a rat, can effectively close the wound and reduce the healing time. Specifically, 280 g of SD rats (purchased from Beijing Vital River) were anesthetized by intraperitoneally injecting 40 mg/kg of sodium pentobarbital, and the skin on the back was shaved and disinfected with iodine tincture. After a 2 cm-long full-thickness incision was made by a scalpel, the hydrogel was applied to the incision, and the incision was closed for 2 min for fully crosslinking. Refer to FIG. 7, FIG. 7 shows the use of the polyethylene glycol hydrogel as prepared in Example 14 of the present invention in the wound closure of rat skin. In FIG. 7, the blank refers to natural healing.

Example 15

The four-arm polyethylene glycol derivative prepared in Example 7 (number-average molecular weight: 10000, 150 mg) was weighed and dissolved in PBS (1 mL) to obtain solution 1. The four-arm polyethylene glycol with amino as terminal group (as shown by Formula Va) (number-average molecular weight: 10000, 150 mg) was weighed and dissolved in PBS (1 mL) to obtain solution 2. Each barrel in the double-barreled syringe was used to draw one solution respectively, and the solutions were simultaneously injected to obtain a hydrogel.

Figure 8:
FIG. 8 shows the use of the polyethylene glycol hydrogel as prepared in Example 15 of the present invention in the sealing and hemostasis of rat liver defect.

The hydrogel prepared in this Example, which was applied to a rat liver defect site, can effectively achieve the sealing and hemostasis. Specifically, 280 g of SD rats (purchased from Beijing Vital River), were intraperitoneally injected with 3000 U/kg of heparin. After 30 min, they were anesthetized by intraperitoneally injecting 40 mg/kg of sodium pentobarbital. The liver was exposed, and a 3 mm-deep incision was made by a scalpel. The hydrogel was applied to the incision, to observe the hemostatic effect. Referring to FIG. 8, FIG. 8 shows the use of the polyethylene glycol hydrogel as prepared in Example 15 of the present invention in the sealing and hemostasis of rat liver defect.

Example 16

The four-arm polyethylene glycol derivative prepared in Example 7 (number-average molecular weight: 10000, 150 mg) was weighed and dissolved in PBS (1 mL) to obtain solution 1. The four-arm polyethylene glycol with amino as terminal group (as shown by Formula Va) (number-average molecular weight: 10000, 150 mg) was weighed and dissolved in PBS (1 mL) to obtain solution 2. Each barrel in the double-barreled syringe was used to draw one solution respectively, and the solutions were simultaneously injected to obtain a hydrogel.

Figure 9:
FIG. 9 shows the use of the polyethylene glycol hydrogel as prepared in Example 16 of the present invention in the sealing and hemostasis of rabbit abdominal aorta defect.

The hydrogel prepared in this Example, which was applied to a rabbit abdominal aorta defect site, can effectively achieve the sealing and hemostasis. Specifically, 3 kg of New Zealand rabbits (purchased from Beijing Vital River), were anesthetized by injecting 40 mg/kg of sodium pentobarbital through the ear vein. The abdominal aorta was exposed, and a 4 mm incision was made by a scalpel. The blood flowing was controlled by the arterial vascular clamp. The hydrogel was applied to the incision, and after 30 seconds for fully crosslinking, the vascular clamp was removed to observe the hemostatic effect. Referring to FIG. 9, FIG. 9 shows the use of the polyethylene glycol hydrogel as prepared in Example 16 of the present invention in the sealing and hemostasis of rabbit abdominal aorta defect.

Comparative Example 1

The preparation method of the four-arm polyethylene glycol with benzaldehyde as terminal group was as follows:
The four-arm polyethylene glycol with benzaldehyde as terminal group (number-average molecular weight: 10000, 2.0 g) was dissolved in 40 mL of dichloromethane, followed by the addition of 1-(3-dimethylaminopropyl)-3-ethylcarbodiimide hydrochloride (1.5 g), 4-dimethylaminopyridine (98 mg), and carboxybenzaldehyde (0.6 g), and the reaction was conducted for 72 h. The reaction solution was washed with saturated brine for 3 times, dried over anhydrous sodium sulfate, filtered, and poured into glacial ethyl ether for settling. The obtained solid was dissolved in water, transferred to a dialysis bag with a molecular weight cut-off of 3500 and dialyzed for 72 h, then lyophilized, to obtain a four-arm polyethylene glycol with benzaldehyde as terminal group (1.5 g, 75%).

The above-mentioned four-arm polyethylene glycol with benzaldehyde as terminal group (number-average molecular weight: 10000, 60 mg) was weighed and dissolved in PBS (1 mL) to obtain solution 1. The four-arm polyethylene glycol with amino as terminal group (as shown by Formula Va) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the hydrogel cannot be formed after 24 h.

The solution 1 (150 μL) and the solution 2 (150 μL) were mixed thoroughly, and then quickly transferred to a rheometer to measure the changes over time of storage modulus and loss modulus for the mixed solution, wherein the elastic modulus of the hydrogel is 0.2 Pa, much lower than that of the hydrogel prepared in Example 11 (13.0 kPa).

Comparative Example 2

The above-mentioned four-arm polyethylene glycol with benzaldehyde as terminal group (number-average molecular weight: 10000, 60 mg) was weighed and dissolved in PBS (1 mL) to obtain solution 1. The four-arm polyethylene glycol with carbazate as terminal group (as shown by Formula Vb) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the gel-forming time is 290 minutes, much higher than that of the hydrogel prepared in Example 12 (290 s).

The solution 1 (150 μL) and the solution 2 (150μL) were mixed thoroughly, and then quickly transferred to a rheometer to measure the changes over time of storage modulus and loss modulus for the mixed solution, wherein the elastic modulus of the hydrogel is 1.3 kPa, much lower than that of the hydrogel prepared in Example 12 (11.1 kPa).

Comparative Example 3

The above-mentioned four-arm polyethylene glycol with benzaldehyde as terminal group (number-average molecular weight: 10000, 60 mg) was weighed and dissolved in PBS (1 mL) to obtain solution 1. The four-arm polyethylene glycol with aminooxy as terminal group (as shown by Formula Ve) (number-average molecular weight: 10000, 60 mg) was weighed and dissolved in PBS (1 mL) to obtain solution 2. The solution 1 (100 μL) and the solution 2 (100 μL) were mixed thoroughly, and placed in a water bath at 37° C. The gelation status was observed by inverted method, and the gel-forming time is 80 minutes, much higher than that of the hydrogel prepared in Example 13 (160 s).

The solution 1 (150 μL) and the solution 2 (150μL) were mixed thoroughly, and then quickly transferred to a rheometer to measure the changes over time of storage modulus and loss modulus for the mixed solution, wherein the elastic modulus of the hydrogel is 6.6 kPa, lower than that of the hydrogel prepared in Example 13 (10.6 kPa).

The above contents are preferred embodiments of the present invention only. It should be pointed out that those of ordinary skill in the art can also make several improvements and modifications without departing from the principle of the present invention. These improvements and modifications should also be regarded as within the protection scope of the present invention.

What is claimed is:

1. A polyethylene glycol derivative, comprising a repeat unit having the structure of Formula (I) and a terminal group having the structure of Formula (II);

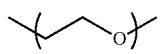
Formula (I)

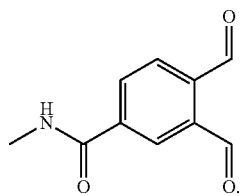
Formula (II)

2. The polyethylene glycol derivative according to claim 1, wherein the polyethylene glycol derivative has any one of the structures of Formula (IIIa), Formula (IIIb), Formula (IIIc), Formula (IIId), and Formula (IIIe):

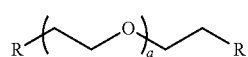
(IIIa)

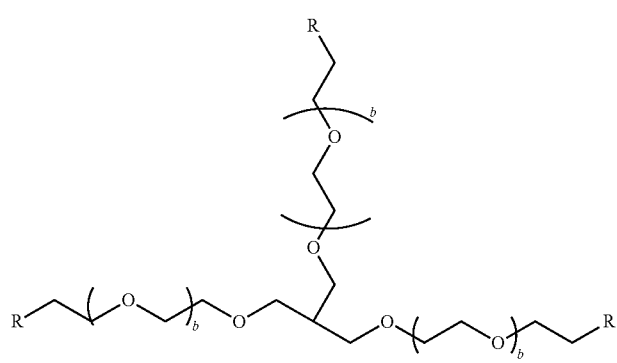
(IIIb)

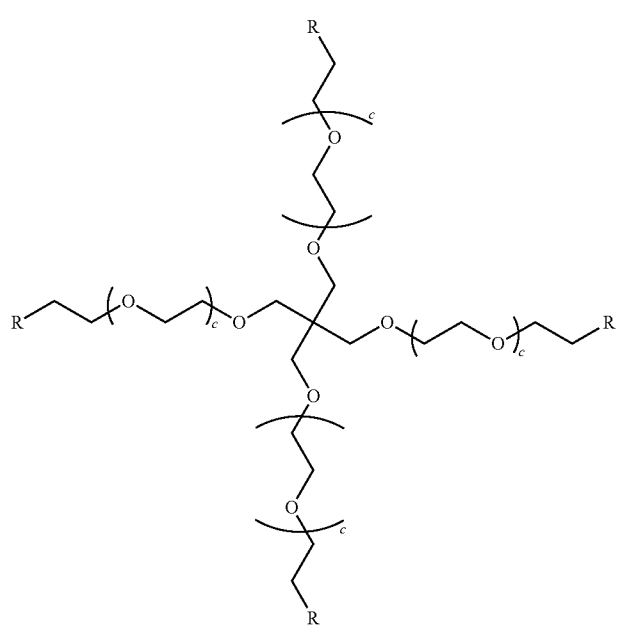
(IIIc)

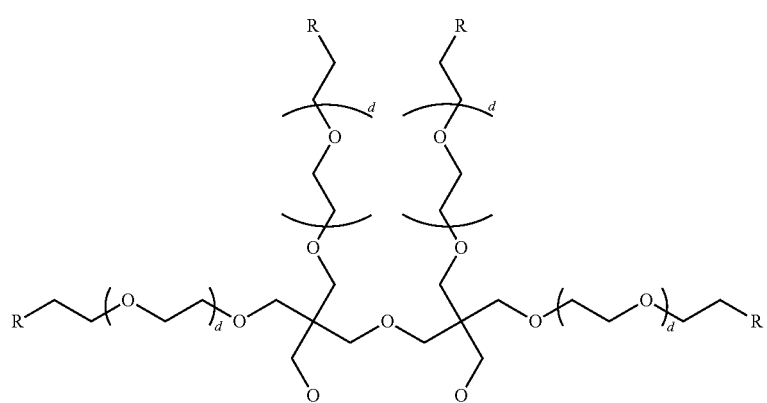

(IIId)

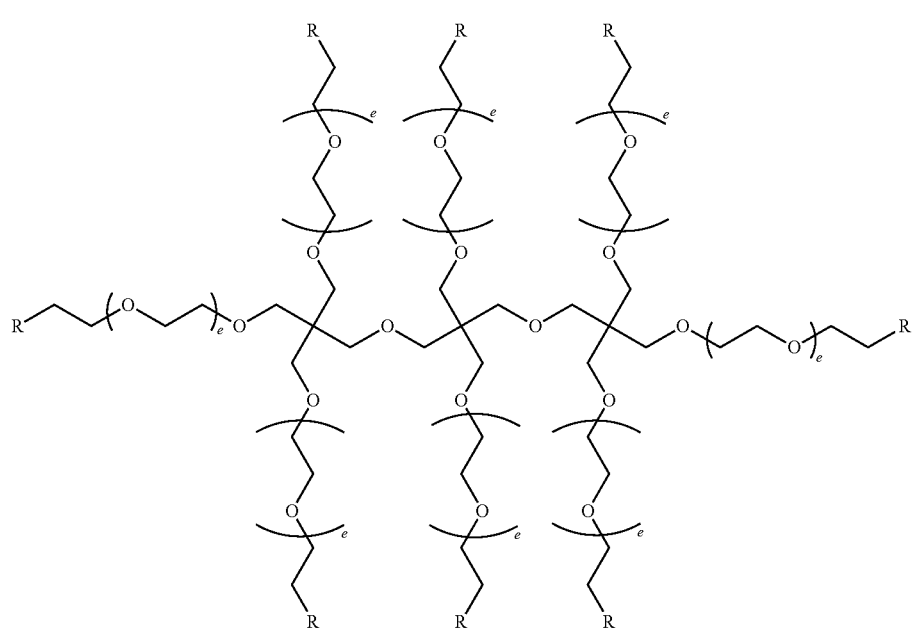

(IIIe)

wherein
 a is the degree of polymerization, $1 \leq a \leq 1000$;
 b is the degree of polymerization, $1 \leq b \leq 333$;
 c is the degree of polymerization, $1 \leq c \leq 250$;
 d is the degree of polymerization, $1 \leq d \leq 166$;
 e is the degree of polymerization, $1 \leq e \leq 125$; and
 R is a terminal group having the structure of Formula (II).

3. A preparation method of the polyethylene glycol derivative according to claim 1, including the following steps:
 A) reacting 1,3-dimethoxy-1,3-dihydroisobenzofuran-5-carboxylic acid succinimidyl ester with a polyethylene glycol having amino as terminal group to obtain a reaction product; and
 B) deprotecting the reaction product to obtain a polyethylene glycol derivative.

4. The preparation method according to claim 3, wherein the 1,3-dimethoxy-1,3-dihydroisobenzofuran-5-carboxylic acid succinimidyl ester is prepared by the following process:
 1) brominating 3,4-dimethylbenzoic acid to prepare 3,4-bis (dibromomethyl) benzoic acid;
 2) hydrolyzing 3,4-bis (dibromomethyl) benzoic acid to obtain 3,4-diformylbenzoic acid;
 3) reacting 3,4-diformylbenzoic acid with methanol to obtain 1,3-dimethoxy-1,3-dihydroisobenzofuran-5-carboxylic acid; and
 4) reacting 1,3-dimethoxy-1,3-dihydroisobenzofuran-5-carboxylic acid with N-hydroxysuccinimide and a condensation agent to obtain 1,3-dimethoxy-1,3-dihydroisobenzofuran-5-carboxylic acid succinimidyl ester.

5. A polyethylene glycol hydrogel which is formed by connecting a polyethylene glycol derivative and a polyethylene glycol having an amino-containing terminal group via a chemical bond, wherein the polyethylene glycol derivative is the polyethylene glycol derivative according to claim 1.

6. The polyethylene glycol hydrogel according to claim 5, wherein the polyethylene glycol having an amino-containing terminal group comprises a repeat unit having the structure of Formula (IV) and a terminal group having any one of the structures of Formula (Va), Formula (Vb), Formula (Vc), Formula (Vd), and Formula (Ve);

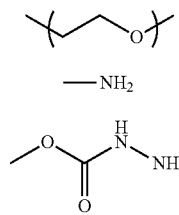
(IV)

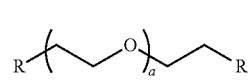
(Va)
(Vb)

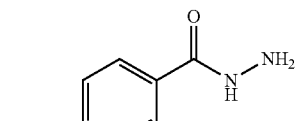
(Vc)

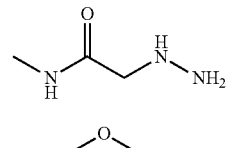
(Vd)

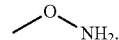
(Ve)

7. The polyethylene glycol hydrogel according to claim 6, wherein the polyethylene glycol having an amino-containing terminal group has any of the structures of Formula (VIa), Formula (VIb), Formula (VIc), Formula (VId), and Formula (VIe):

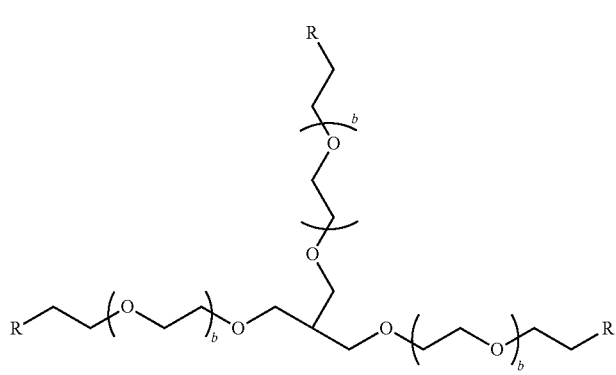
(VIa)
(VIb)

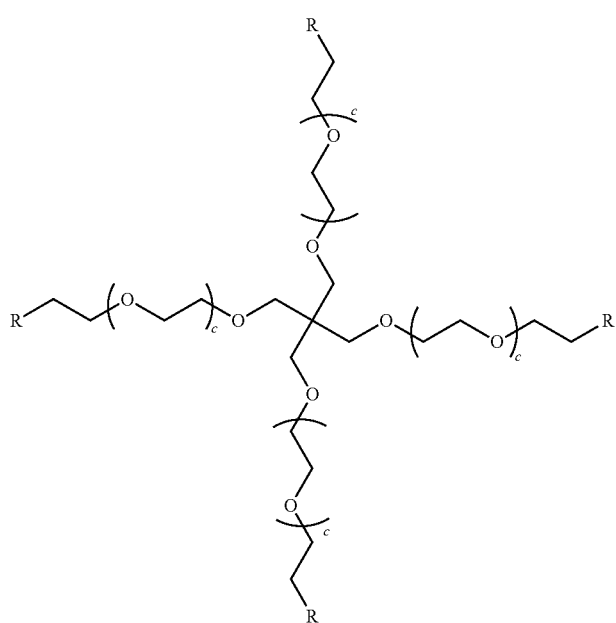
(VIc)

-continued

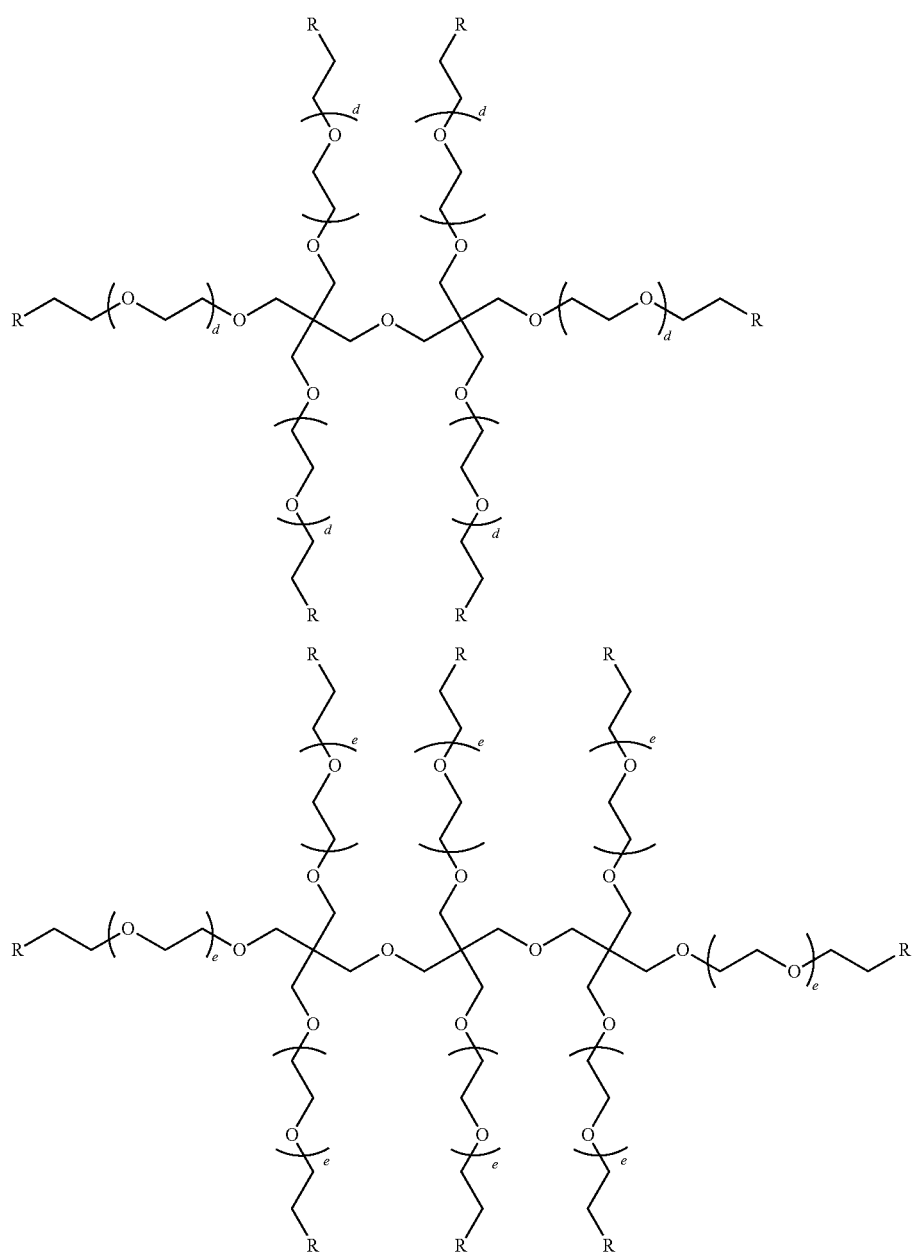

wherein
   a is the degree of polymerization, $1 \leq a \leq 1000$;
   b is the degree of polymerization, $1 \leq b \leq 333$;
   c is the degree of polymerization, $1 \leq c \leq 250$;
   d is the degree of polymerization, $1 \leq d \leq 166$;
   e is the degree of polymerization, $1 \leq e \leq 125$; and
   R is a terminal group having any of the structures of Formula (Va), Formula (Vb), Formula (Vc), Formula (Vd), and Formula (Ve).

8. A preparation method of the polyethylene glycol hydrogel according to claim 5, wherein the polyethylene glycol hydrogel is prepared from the polyethylene glycol derivative, the polyethylene glycol having the amino-containing terminal group, and a solvent.

9. The preparation method according to claim 8, wherein the solvent is water, physiological saline, or buffer solution; the polyethylene glycol derivative has a mass-volume concentration of 1~1000 mg/ml; and the polyethylene glycol having the amino-containing terminal group has a mass-volume concentration of 1~1000 mg/mL.

10. The preparation method according to claim 8, wherein the mass ratio of the polyethylene glycol derivative to the polyethylene glycol having the amino-containing terminal group is 1:0.01~100.

* * * * *